United States Patent [19]

Kubota et al.

[11] Patent Number: 5,451,693
[45] Date of Patent: Sep. 19, 1995

[54] TERT-BUTYL CYCLOALKYL DIALKOXYSILANE COMPOUNDS AND METHOD FOR PREPARING SAME

[75] Inventors: Tohru Kubota; Akira Yamamoto, both of Niigata; Muneo Kudo, Gunma, all of Japan

[73] Assignee: Shin-Etsu Chemical Co., Ltd., Tokyo, Japan

[21] Appl. No.: 301,880

[22] Filed: Sep. 7, 1994

[30] Foreign Application Priority Data

Sep. 10, 1993 [JP] Japan ................ 5-225344

[51] Int. Cl.⁶ .............................................. C07F 7/18
[52] U.S. Cl. ...................................................... 556/482
[58] Field of Search ........................................ 556/482

[56] References Cited

U.S. PATENT DOCUMENTS

| | | | |
|---|---|---|---|
| 4,956,484 | 9/1990 | Gementi et al. | 556/482 X |
| 5,142,082 | 8/1992 | Sato et al. | 556/482 |
| 5,175,332 | 12/1992 | Chatterton et al. | 556/482 |
| 5,248,803 | 9/1993 | Aoki et al. | 556/482 |
| 5,296,624 | 3/1994 | Larson et al. | 556/482 X |
| 5,359,114 | 10/1994 | Aoki et al. | 556/482 |

FOREIGN PATENT DOCUMENTS

| | | |
|---|---|---|
| 0376084 | 7/1990 | European Pat. Off. |
| 0452916A1 | 10/1991 | European Pat. Off. |
| 0460590A1 | 12/1991 | European Pat. Off. |
| 0488759A1 | 6/1992 | European Pat. Off. |

OTHER PUBLICATIONS

Chemical Abstracts, vol. 119, No. 8 (Aug. 23, 1993), Abstract No. 73312 p. (Dec. 1989).

*Primary Examiner*—Paul F. Shaver, Sr.
*Attorney, Agent, or Firm*—Sughrue, Mion, Zinn, Macpeak & Seas

[57] ABSTRACT

Herein disclosed are a tert-butyl cycloalkyl dialkoxysilane compound which is quite useful as a water repellant for treating the surface of a variety of construction materials such as wood, concrete and marble and which can easily be used, and a method for preparing the compound. A Grignard reagent represented by the formula: $R^1MgX$ is reacted with a silane compound represented by the formula: $(CH_3)_3CSiH(OR^2)_2$. Then the resulting silane compound: $(CH_3)_3CSiHR^1(OR^2)$ is further reacted with an alcohol: $R^2OH$ in the presence of a catalyst to give a tert-butyl cycloalkyl dialkoxysilane compound: $(CH_3)_3CSiR^1(OR^2)_2$.

7 Claims, 2 Drawing Sheets

TERT-BUTYL CYCLOALKYL DIALKOXYSILANE COMPOUNDS AND METHOD FOR PREPARING SAME

BACKGROUND OF THE INVENTION

The present invention relates to a novel silane compound and a method for preparing the compound. The silane compound is useful as a water repellant for treating the surface of a variety of construction materials such as wood, concrete and marble.

It has been known that alkoxysilane compounds carrying linear alkyl groups are useful as water repellents for imparting water repellency to the surface of a variety of construction materials such as wood, concrete and marble. The longer and bulkier the alkyl chain of an alkoxysilane compound is, the higher the water repellency of the compound. However, a silane compound having a long chain alkyl group has a high melting point or a high boiling point and the alkyl group of the silane compound should accordingly be limited in its chain length from the viewpoint of the production and use thereof. For this reason, a need has been existing for the development of a bulky substituent-carrying alkoxysilane compound which can easily be prepared and can easily be handled.

On the other hand, it has also been known that an alkoxysilane compound having a bulky and less flexible substituent is useful as a silane coupling agent or a component of a catalyst for polymerizing olefinic monomers. Under such circumstances, a need has been existing for the development of a novel alkoxysilane compound having a bulky and less flexible substituent.

SUMMARY OF THE INVENTION

An object of the present invention is generally to solve the foregoing problems associated with the conventional techniques and more specifically to provide a novel alkoxysilane compound which has a bulky and less flexible substituent and a hydrolyzable Si-OCH$_3$ group as well as tert-butyl and cycloalkyl groups as alkyl groups and which can easily be prepared and handled and to provide a method for industrially easily preparing the alkoxysilane compound.

According to the present invention, a Grignard reagent represented by the following general formula: $R^1MgX$ is reacted with a silane compound represented by the following general formula: $(CH_3)_3CSiH(OR^2)_2$ and then the resulting silane compound: $(CH_3)_3CSiHR^1OR^2$ is further reacted with an alcohol: $R^2OH$ in the presence of a catalyst to give a tert-butyl cycloalkyl dialkoxysilane compound represented by the formula: $(CH_3)_3CSiR^1(OR^2)_2$.

The method of the present invention allows the easy preparation of a novel alkoxysilane compound having a bulky substituent. The alkoxysilane compound can easily be handled when put into practical use.

DETAILED DESCRIPTION OF THE INVENTION

Figure 1:
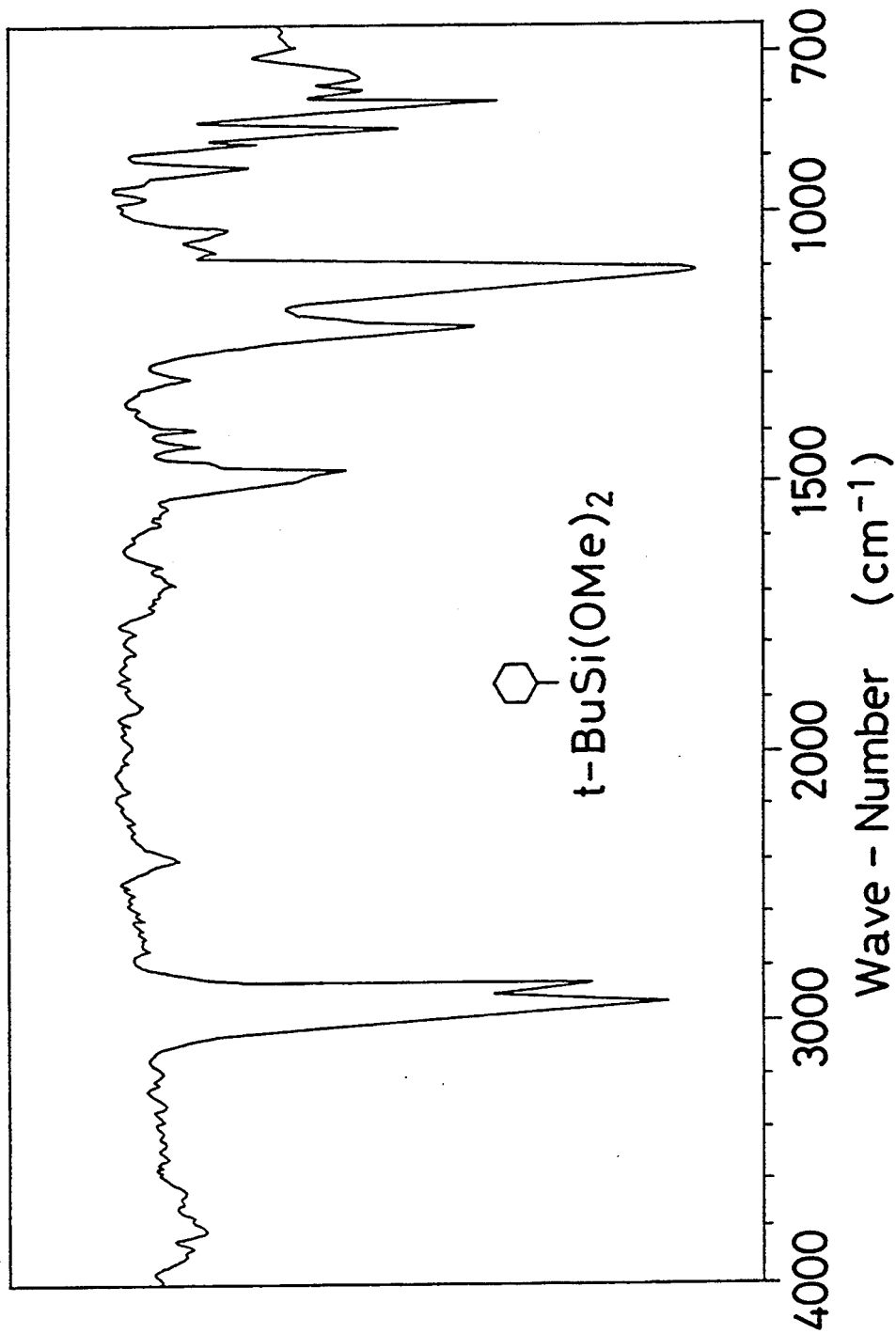
FIG. 1 is a chart showing the infrared absorption spectrum of the silane compound prepared in an example of the method according to the present invention.

The silane compound according to the present invention is a tert-butyl cycloalkyl dialkoxysilane compound represented by the following general formula (I):

$$(CH_3)_3CSiR^1(OR^2)_2 \qquad (I)$$

In Formula (I), $R^1$ represents a cycloalkyl group having 5 to 7 carbon atoms; and $R^2$ represents a methyl or ethyl group.

The tert-butyl cycloalkyl dialkoxysilane compound represented by Formula (I) is prepared in accordance with the following method.

A Grignard reagent represented by the following general formula (II):

$$R^1MgX \qquad (II)$$

is reacted with a silane compound represented by the following general formula (III):

$$(CH_3)_3CSiH(OR^2)_2 \qquad (III)$$

and then the resulting silane compound represented by the following general formula (IV):

$$(CH_3)_3CSiHR^1(OR^2) \qquad (IV)$$

is further reacted with an alcohol represented by the following general formula (V):

$$R^2OH \qquad (V)$$

in the presence of a catalyst. In the chemical formulas (II) to (V), $R^1$ and $R^2$ are the same as those defined above in connection with the chemical formula (I) and X appearing in the chemical formula (II) represents a halogen atom.

Specific examples of the Grignard reagents represented by Chemical Formula (II) include cyclopentyl magnesium chloride, cyclopentyl magnesiumbromide, cyclohexyl magnesium chloride, cyclohexyl magnesiumbromide, cyclohexyl magnesium iodide, cycloheptyl magnesium chloride and cycloheptyl magnesium bromide. A method for preparing the Grignard reagent of Formula (II) comprises the step of reacting a cycloalkyl halide with elemental magnesium in an ether solvent such as diethyl ether or tetrahydrofuran.

The tert-butyl dialkoxysilane compound represented by Chemical Formula (III) may be, for instance, tert-butyl dimethoxysilane or tert-butyl diethoxysilane. Methods for preparing these compounds are disclosed in, for instance, Japanese Un-examined Patent Publication No. Sho 62-22790.

Specific examples of the tert-butyl cycloalkyl alkoxysilane compounds represented by Chemical Formula (IV) are tert-butylcyclopentyl methoxysilane, tert-butyl cyclopentyl ethoxysilane, tert-butyl cyclohexyl methoxysilane, tert-butyl cyclohexyl ethoxysilane, tert-butyl cycloheptyl methoxysilane and tert-butyl cycloheptyl ethoxysilane. A method for preparing the tert-butyl cycloalkyl alkoxysilane compounds of Formula (IV) comprises the step of reacting a Grignard reagent of Formula (II) with a tert-butyl dialkoxysilane compound (III). In this reaction, the Grignard reagent is used in an amount ranging from 0.9 to 1.1 mole eq. on the basis of the amount of the tert-butyl dialkoxysilane compound. The reaction is desirably carried out at a temperature ranging from 0° to 100° C. and preferably 20° to 80° C.

The alcohol represented by Chemical Formula (V) may be methanol or ethanol.

The novel silane compound represented by Chemical Formula(I) according to the present invention may be, for instance, tert-butyl cyclopentyl dimethoxysilane, tert-butyl cyclopentyl diethoxysilane, tert-butyl cyclohexyl dimethoxysilane and tert-butyl cyclohexyl diethoxysilane. The novel silane compound of Formula (I) is prepared by reacting a tert-butyl cycloalkyl alkoxysilane compound of Formula (IV) with an alcohol of Formula (V) in the presence of a catalyst. Examples of the catalysts usable in this reaction are palladium complexes with metal alkoxides such as sodium methoxide and sodium ethoxide; transition metals such as rhodium and platinum; and metal compounds such as palladium acetate, chlorotristriphenylphosphine rhodium and chloroplatinic acid. These catalysts are desirably used in an amount ranging from 0.01 to 10 mole % and preferably 0.1 to 1 mole % on the basis of the molar amount of the tert-butyl cycloalkyl alkoxysilane compound. The alcohol is used in an amount ranging from 1 to 10 mole eq. on the basis of the amount of the tert-butyl cycloalkyl alkoxysilane compound. The reaction is desirably carried out at a temperature around the boiling point of the alcohol used.

Working Examples of the present invention will be detailed below.

Example 1

To a 500 ml volume flask equipped with a stirring machine, a reflux condenser, a thermometer and a dropping funnel, there were added 12.2 g (0.5 mole) of elemental magnesium, 150 ml of tetrahydrofuran and a small amount of iodine, followed by dropwise addition of 59.3 g (0.5 mole) of cyclohexyl magnesium chloride through the dropping funnel in a nitrogen gas atmosphere at a temperature of the contents ranging from 40° to 50° C. over one hour and stirring at 55° C. for additional one hour to give cyclohexyl magnesiumchloride as a Grignard reagent. To another 500 ml volume flask equipped with a stirring machine, a reflux condenser, a thermometer and a dropping funnel, there were added 74.1 g (0.5 mole) of tert-butyl dimethoxysilane and 100 ml of tetrahydrofuran, followed by dropwise addition of the foregoing cyclohexylmagnesium chloride through the dropping funnel in a nitrogen gas atmosphere at a temperature of the contents ranging from 30° to 40° C. over one hour and stirring the contents at a temperature ranging from 70° to 80° C. for additional one hour. After filtering the reaction solution under a reduced pressure, the solution was distilled to recover a cut boiling at 89° to 91° C./10 mmHg and to thus give 79.2 g of a compound.

To a still another 200 ml volume flask equipped with a stirring machine, a reflux condenser, a thermometer and a dropping funnel, there were added 64.0 g of methanol and 0.43 g (8.0 mM) of sodium methoxide as a catalyst, followed by dropwise addition of the foregoing compound (79.2 g) obtained by the foregoing distillation through the dropping funnel at a temperature ranging from 60° to 70° C. over one hour and stirring for 3 hours. The reaction solution was distilled to give 81.8 g of a compound having a boiling point of 91°–93° C./2 mmHg. The yield was found to be 71%.

The substance thus obtained was subjected to determination of the mass spectrum (MS), nuclear magnetic resonance spectrum(NMR) and infrared absorption spectrum (IR).

The results of the mass spectrum (MS) measurement are as follows.

Mass Spectrum (MS): m/z (attribution) 230 (peak of a molecular ion (M+)) 173 (peak of M+—C(CH$_3$)$_3$ ion)

The results of the nuclear magnetic resonance spectrum (NMR) measurement are shown in Table 1. Table 1 shows the positions of chemical shifts observed for the hydrogen atoms of the novel silane compound.

Nuclear Magnetic Resonance Spectrum (NMR): σ(ppm)

TABLE 1

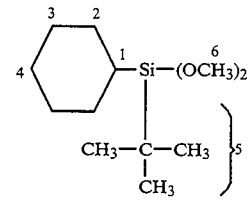

| No. | Chemical Shift (ppm) |
| --- | --- |
| 1 | 0.87 |
| 2ax: axial proton | 1.00 to 1.37 |
| 2eq: equatorial proton | 1.56 to 1.83 |
| 3ax: axial proton | 1.00 to 1.37 |
| 3eq: equatorial proton | 1.56 to 1.83 |
| 4ax: axial proton | 1.00 to 1.37 |
| 4eq: equatorial proton | 1.56 to 1.83 |
| 5 | 0.90 |
| 6 | 3.53 |

The results of the infrared absorption spectrum (IR) measurement are shown in FIG. 1. FIG. 1 is a spectrum chart observed for the novel silane compound.

From the foregoing results of the spectral analysis, the compound thus prepared was confirmed to be tert-butyl cyclohexyl dimethoxysilane.

Example 2

The same procedures used in Example 1 were repeated except that 52.3 g (0.5 mole) of cyclopentyl chloride was substituted for 59.3 g (0.5 mole) of the cyclohexyl chloride used in Example 1 to give a Grignard reagent which was subsequently reacted with tert-butyl dimethoxysilane in the same manner used in Example 1. After filtering the reaction solution under a reduced pressure, the solution was distilled to recover a cut boiling at 73° to 75° C./10 mmHg and to thus give 76.4 g of a compound.

To another 200 ml volume flask equipped with a stirring machine, a reflux condenser, a thermometer and a dropping funnel, there were added 65.7 g of methanol and 0.45 g (8.3 mM) of sodium methoxide as a catalyst, followed by dropwise addition of the foregoing compound (76.4 g) obtained by the foregoing distillation through the dropping funnel at a temperature ranging from 60° to 70° C. over one hour and stirring for 3 hours. The reaction solution was distilled to give 80.1 g of a compound having a boiling point of 90°–91° C./5 mmHg. The yield was found to be 74%.

The substance thus obtained was subjected to measurement of the mass spectrum (MS), nuclear magnetic resonance spectrum (NMR) and infrared absorption spectrum (IR).

The results of the mass spectrum (MS) measurement are as follows.

Mass Spectrum (MS): m/z (attribution) 216 (peak of a molecular ion (M+)) 159 (peak of M+—CH₃ ion)

The results of the nuclear magnetic resonance spectrum (NMR) measurement are shown in Table 2. Table 2 shows the positions of chemical shifts observed for the hydrogen atoms of the novel silane compound.

Nuclear Magnetic Resonance Spectrum (NMR): σ(ppm)

TABLE 2

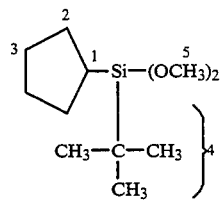

| No. | Chemical Shift (ppm) |
|-----|----------------------|
| 1   | 1.01                 |
| 2   | 1.30 to 1.87         |
| 3   | 1.30 to 1.65         |
| 4   | 0.89                 |
| 5   | 3.53                 |

Figure 2:
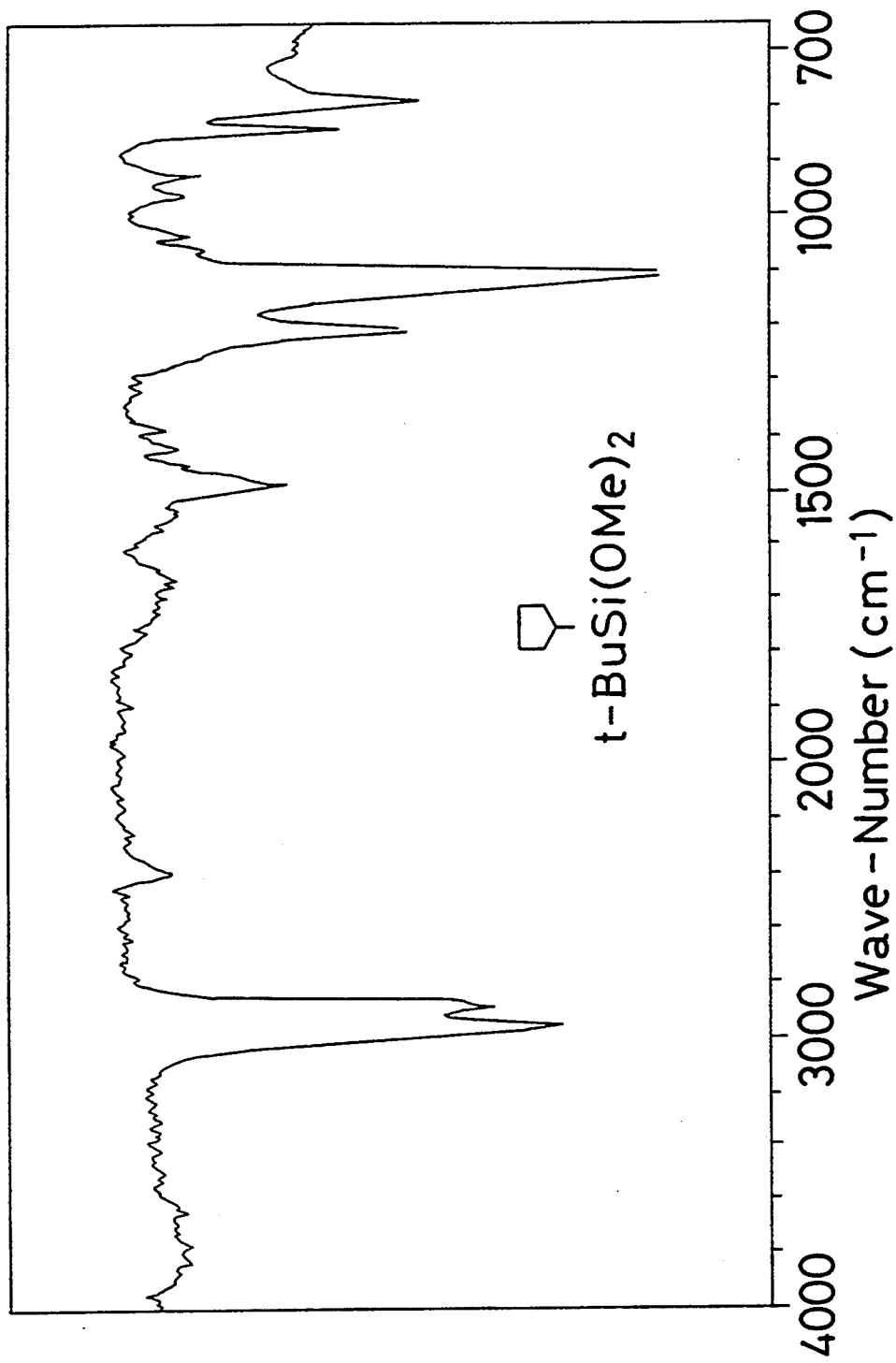
FIG. 2 is a chart showing the infrared absorption spectrum of the silane compound prepared in another example of the method according to the present invention.

The results of the infrared absorption spectrum (IR) measurement are shown in FIG. 2. FIG. 2 is a spectrum chart observed for the novel silane compound. From the foregoing results of the spectral analysis, the compound thus prepared was confirmed to be tert-butyl cyclopentyl dimethoxysilane.

What is claimed is:

1. A tert-butyl cycloalkyl dialkoxysilane compound represented by the following general formula (I):

(CH₃)₃CSiR¹(OR²)₂      (I)

(wherein R¹ represents a cycloalkyl group having 5 to 7 carbon atoms; and R² represents a methyl or ethyl group).

2. The tert-butyl cycloalkyl dialkoxysilane compound as set forth in claim 1 wherein R1 represents a cyclopentyl group, a cyclohexyl group or a cycloheptyl group.

3. A method for preparing a tert-butyl cycloalkyl dialkoxysilane compound represented by the following general formula:

(CH₃)₃CSiR¹(OR²)₂

(wherein R¹ represents a cycloalkyl group having 5 to 7 carbon atoms; and R² represents a methyl or ethyl group) comprising the steps of reacting a Grignard reagent represented by the following general formula (II):

R¹MgX      (II)

(wherein R¹ is the same as that defined above; and X represents a halogen atom) with a silane compound represented by the following general formula (III):

(CH₃)₃CSiH(OR²)₂      (III)

(wherein R² is the same as that defined above) and then reacting the resulting silane compound represented by the following general formula (IV):

(CH₃)₃CSiHR¹OR²      (IV)

(wherein R¹ and R² are the same as those defined above) with an alcohol represented by the following general formula (V):

R²OH      (V)

in the presence of a catalyst.

4. The method for preparing a tert-butyl cycloalkyl dialkoxysilane compound as set forth in claim 3 wherein R1 represents a cyclopentyl group, a cyclohexyl group or a cycloheptyl group.

5. The method for preparing a tert-butyl cycloalkyl dialkoxysilane compound as set forth in claim 3 or 4 wherein the Grignard reagent: R¹MgX is selected from the group consisting of cyclopentyl magnesium chloride, cyclopentyl magnesium bromide, cyclohexyl magnesium chloride, cyclohexyl magnesium bromide, cyclohexyl magnesium iodide, cycloheptyl magnesium chloride and cycloheptyl magnesium bromide.

6. The method for preparing a tert-butyl cycloalkyl dialkoxysilane compound as set forth in claim 3 or 4 wherein the catalyst is a member selected from the group consisting of palladium complexes with metal alkoxides selected from the group consisting of sodium methoxide and sodium ethoxide; transition metals selected from the group consisting of rhodium and platinum; and metal compounds selected from the group consisting of palladium acetate, chlorotristri-phenylphosphine rhodium and chloroplatinic acid.

7. The method for preparing a tert-butyl cycloalkyl dialkoxysilane compound as set forth in claim 5 wherein the catalyst is a member selected from the group consisting of palladium complexes with metal alkoxides selected from the group consisting of sodium methoxide and sodium ethoxide; transition metals selected from the group consisting of rhodium and platinum; and metal compounds selected from the group consisting of palladium acetate, chlorotristri-phenylphosphine rhodium and chloroplatinic acid.

* * * * *